US012048423B2

(12) United States Patent
McGillicuddy et al.

(10) Patent No.: US 12,048,423 B2
(45) Date of Patent: Jul. 30, 2024

(54) BONE MARROW HARVESTING NEEDLE IMPROVEMENTS

(71) Applicant: Cervos Medical LLC, Marshfield, MA (US)

(72) Inventors: Andrew McGillicuddy, Humarock, MA (US); Andy H. Levine, Newton Highlands, MA (US)

(73) Assignee: Cervos Medical LLC, Avon, MA (US)

( * ) Notice: Subject to any disclaimer, the term of this patent is extended or adjusted under 35 U.S.C. 154(b) by 129 days.

(21) Appl. No.: 17/933,734

(22) Filed: Sep. 20, 2022

(65) Prior Publication Data

US 2023/0112782 A1    Apr. 13, 2023

Related U.S. Application Data

(60) Continuation of application No. 16/732,630, filed on Jan. 2, 2020, now Pat. No. 11,478,231, which is a
(Continued)

(51) Int. Cl.
*A61B 10/02* (2006.01)
*A61M 1/00* (2006.01)
(Continued)

(52) U.S. Cl.
CPC ............ *A61B 10/025* (2013.01); *A61M 1/85* (2021.05); *A61M 1/86* (2021.05);
(Continued)

(58) Field of Classification Search
CPC ......... A61B 10/025; A61B 2010/0258; A61M 1/86
See application file for complete search history.

(56) References Cited

U.S. PATENT DOCUMENTS

| 87 A | 11/1836 | Card |
| 3,893,445 A | 7/1975 | Hofsess |

(Continued)

FOREIGN PATENT DOCUMENTS

| WO | WO 2006/027549 A1 | 3/2006 |
| WO | WO 2010/138895 A3 | 2/2010 |

(Continued)

OTHER PUBLICATIONS

Al-Ibraheemi et al., "Comparison between 1-needle technique versus 2-needle technique for bone marrow aspiration and biopsy procedures," Arch Pathol Lab Med., 137(7): 974-8, Jul. 2013.
(Continued)

*Primary Examiner* — Christian A Sevilla
(74) *Attorney, Agent, or Firm* — Hamilton, Brook, Smith & Reynolds, P.C.

(57) ABSTRACT

A bone marrow aspiration device and associated method includes an introducer needle assembly and an aspiration needle assembly. The introducer needle assembly includes an introducer cannula having proximal and distal ends, each end including an opening, and a screw assembly coupled to the introducer handle. The screw assembly includes a threaded tube and a lead screw receivable in the threaded tube. An outer cover is disposed around and in sealing engagement with the threaded tube and the lead screw. The aspiration needle assembly is receivable in the introducer cannula and includes an aspiration cannula forming a channel for aspirating bone marrow and including a flexible portion that extends from a distal end along a length of the aspiration cannula. A length of the aspiration cannula that extends beyond the distal end of the introducer cannula is adjustable by advancing the lead screw into or reversing the lead screw out of the threaded tube.

14 Claims, 12 Drawing Sheets

Related U.S. Application Data division of application No. 15/110,520, filed as application No. PCT/US2015/011614 on Jan. 15, 2015, now Pat. No. 10,556,046.

(60) Provisional application No. 61/986,391, filed on Apr. 30, 2014, provisional application No. 61/950,303, filed on Mar. 10, 2014, provisional application No. 61/927,614, filed on Jan. 15, 2014.

(51) Int. Cl.
*A61B 17/34* (2006.01)
*A61B 90/00* (2016.01)

(52) U.S. Cl.
CPC ........... *A61B 2010/0258* (2013.01); *A61B 2017/3443* (2013.01); *A61B 2090/034* (2016.02); *A61M 2205/586* (2013.01)

(56) References Cited

U.S. PATENT DOCUMENTS

| | | | |
|---|---|---|---|
| 4,010,737 A | 3/1977 | Vilaghy et al. | |
| 4,099,518 A | 7/1978 | Baylis et al. | |
| 4,142,517 A | 3/1979 | Stavropoulos et al. | |
| 4,249,541 A | 2/1981 | Pratt | |
| 4,262,676 A | 4/1981 | Jamshidi | |
| 4,356,828 A | 11/1982 | Jamshidi | |
| 4,366,822 A | 1/1983 | Altshuler | |
| 4,469,109 A | 9/1984 | Mehl | |
| 4,487,209 A | 12/1984 | Mehl | |
| 4,630,616 A | 12/1986 | Tretinyak | |
| 4,649,918 A | 3/1987 | Pegg et al. | |
| 4,793,363 A | 12/1988 | Ausherman et al. | |
| 4,838,282 A | 6/1989 | Strasser et al. | |
| 5,026,350 A | 6/1991 | Tanaka et al. | |
| 5,027,827 A | 7/1991 | Cody et al. | |
| 5,257,632 A | 11/1993 | Turkel et al. | |
| 5,279,306 A | 1/1994 | Mehl | |
| 5,331,972 A | 7/1994 | Wadhwani et al. | |
| 5,357,974 A | 10/1994 | Baldridge | |
| 5,368,046 A | 11/1994 | Scarfone et al. | |
| 5,429,138 A | 7/1995 | Jamshidi | |
| 5,522,398 A | 6/1996 | Goldenberg et al. | |
| 5,526,821 A | 6/1996 | Jamshidi | |
| 5,807,275 A | 7/1998 | Jamshidi | |
| 5,807,276 A | 9/1998 | Russin | |
| 5,833,628 A | 11/1998 | Yuan et al. | |
| 5,954,671 A | 9/1999 | O'Neill | |
| 6,007,496 A | 12/1999 | Brannon | |
| 6,063,037 A | 5/2000 | Mittermeier et al. | |
| 6,080,115 A | 6/2000 | Rubinstein | |
| 6,090,121 A | 7/2000 | Weber et al. | |
| 6,110,128 A | 8/2000 | Andelin et al. | |
| 6,264,618 B1 | 7/2001 | Landi et al. | |
| 6,302,852 B1 | 10/2001 | Fleming et al. | |
| 6,312,394 B1 | 11/2001 | Fleming | |
| 6,416,484 B1 | 7/2002 | Miller et al. | |
| 6,425,887 B1 | 7/2002 | McGuckin et al. | |
| 6,478,751 B1 | 11/2002 | Krueger et al. | |
| 6,554,778 B1 | 4/2003 | Fleming | |
| 6,554,803 B1 | 4/2003 | Ashman | |
| 6,730,043 B2 | 5/2004 | Krueger et al. | |
| 6,755,793 B2 | 6/2004 | Lamoureux et al. | |
| 6,849,051 B2 | 2/2005 | Sramek et al. | |
| 6,905,489 B2 | 6/2005 | Mantell et al. | |
| 6,916,292 B2 | 7/2005 | Morawski et al. | |
| 6,981,948 B2 | 1/2006 | Pellegrino et al. | |
| 7,081,123 B2 | 7/2006 | Merboth et al. | |
| 7,179,232 B2 | 2/2007 | Sutton et al. | |
| 7,278,972 B2 | 10/2007 | Lamoureux et al. | |
| 7,462,181 B2 | 12/2008 | Kraft et al. | |
| 7,637,872 B1 | 12/2009 | Fox | |
| 7,850,651 B2 | 12/2010 | Allee et al. | |
| 8,043,253 B2 | 10/2011 | Kraft et al. | |
| 8,343,133 B2 | 1/2013 | Allee et al. | |
| 9,017,298 B2 | 4/2015 | Allee et al. | |
| 9,078,638 B2 * | 7/2015 | Wuestemann | A61B 10/025 |
| 9,226,732 B2 * | 1/2016 | Azimpoor | A61B 10/025 |
| 9,402,602 B2 * | 8/2016 | Lee | A61B 10/0233 |
| 10,231,716 B2 | 3/2019 | McGillicuddy et al. | |
| 10,568,661 B2 | 2/2020 | McGillicuddy | |
| 10,556,046 B2 | 11/2020 | McGillicuddy | |
| 10,820,913 B2 * | 11/2020 | Miller | A61B 10/025 |
| 10,993,707 B2 | 5/2021 | McGillicuddy | |
| 11,020,097 B2 * | 6/2021 | Morgan | A61B 10/025 |
| 11,039,817 B2 | 6/2021 | McGillicuddy | |
| 11,497,480 B2 | 11/2022 | McGillicuddy et al. | |
| 11,564,669 B2 | 1/2023 | McGillicuddy | |
| 11,576,659 B2 | 2/2023 | McGillicuddy | |
| 11,918,193 B2 | 3/2024 | McGillicuddy | |
| 2001/0001811 A1 | 5/2001 | Burney et al. | |
| 2003/0050574 A1 | 3/2003 | Krueger | |
| 2003/0233114 A1 | 12/2003 | Merboth et al. | |
| 2004/0077973 A1 | 4/2004 | Groenke et al. | |
| 2004/0127814 A1 * | 7/2004 | Negroni | A61B 10/025 600/567 |
| 2004/0153005 A1 | 8/2004 | Krueger | |
| 2004/0191897 A1 | 9/2004 | Muschler | |
| 2004/0267154 A1 | 12/2004 | Sutton et al. | |
| 2006/0247552 A1 | 11/2006 | Ikehara et al. | |
| 2006/0276747 A1 | 12/2006 | Moos et al. | |
| 2007/0016100 A1 | 1/2007 | Miller | |
| 2007/0055282 A1 | 3/2007 | Muschler | |
| 2007/0066987 A1 | 3/2007 | Scanlan, Jr. et al. | |
| 2007/0198043 A1 | 8/2007 | Cox et al. | |
| 2007/0293788 A1 | 12/2007 | Entrekin et al. | |
| 2008/0045857 A1 | 2/2008 | Miller et al. | |
| 2008/0214957 A1 | 9/2008 | Verra et al. | |
| 2009/0149774 A1 | 6/2009 | Simon et al. | |
| 2010/0069843 A1 | 3/2010 | Allee et al. | |
| 2010/0280410 A1 | 11/2010 | Moos et al. | |
| 2011/0082425 A1 | 4/2011 | Wuestemann et al. | |
| 2011/0112436 A1 | 5/2011 | Jones et al. | |
| 2011/0224576 A1 | 9/2011 | Jackson et al. | |
| 2012/0035501 A1 | 2/2012 | Landrigan et al. | |
| 2012/0116247 A1 | 5/2012 | Wawrzyniak et al. | |
| 2012/0129676 A1 | 5/2012 | Duffy et al. | |
| 2012/0136277 A1 | 5/2012 | Landrigan et al. | |
| 2013/0131545 A1 | 5/2013 | Azimpoor et al. | |
| 2013/0150752 A1 | 6/2013 | Swann | |
| 2014/0081318 A1 | 3/2014 | Houser et al. | |
| 2015/0289858 A1 | 10/2015 | McGillicuddy et al. | |
| 2016/0106462 A1 | 4/2016 | McGillicuddy et al. | |
| 2016/0331878 A1 | 11/2016 | McGillicuddy et al. | |
| 2018/0085144 A1 | 3/2018 | McGillicuddy | |
| 2019/0314004 A1 | 10/2019 | McGillicuddy et al. | |
| 2020/0205792 A1 | 2/2020 | McGillicuddy | |
| 2020/0129680 A1 | 4/2020 | McGillicuddy | |
| 2020/0305930 A1 | 10/2020 | McGillicuddy | |
| 2021/0038201 A1 | 2/2021 | McGillicuddy | |
| 2021/0315553 A1 | 10/2021 | McGillicuddy | |
| 2023/0072916 A1 | 3/2023 | McGillicuddy et al. | |
| 2023/0389906 A1 | 12/2023 | McGillicuddy | |

FOREIGN PATENT DOCUMENTS

| | | |
|---|---|---|
| WO | WO 2010/138895 A2 | 12/2010 |
| WO | WO 2012/047984 A1 | 4/2012 |
| WO | WO 2013/096419 A1 | 6/2013 |
| WO | WO 2014/070804 A1 | 5/2014 |
| WO | WO 2015/109100 A1 | 7/2015 |

OTHER PUBLICATIONS

Bhootra, B.L. "1. Fatality Following a Sternal Bone Marrow Aspiration Procedure," Medicine, Science and the Law. 2004;44(2):170-172. doi:10.1258/rsmmsl.44.2.170, 2004.
Definition of offset (Dictionary.com on Jun. 4, 2018).
Harrell, D.V., et al., "Novel Technology to Increase Concentrations of Stem and Progenitor Cells in Marrow Aspiration," downloaded from www.marrowcellutions.com on Oct. 7, 2015 (8 pages).

(56) References Cited

OTHER PUBLICATIONS

Hernigou et al., "Percutaneous Autologous Bone-Marrow Grafting for Nonunions. Surgical Technique," The Journal of Bone and Joint Surgery, Inc., vol. 88-A1, Supplement 1, Part 2, Sep. 2006.
Islam, A., "Bone marrow aspiration before bone marrow core biopsy using the same bone marrow biopsy needle: a good or bad practice?," J Clin Pathol., 60(2): 212-215, Feb. 2007.
Islam, A., "New sternal puncture needle," J. Clin. Pathol, 44, pp. 690-691, 1991.
Malempati et al., "Bone marrow aspiration and biopsy," N. Engl J. Med. 36(15), NEJM.org, 2009.
Muschler et al., "Aspiration to Obtain Osteoblast Progenitor Cells from Human Bone Marrow: The Influence of Aspiration Volume," The Journal of Bone and Joint Surgery, Inc., vol. 79-A, No. 11, Nov. 1997.
Ranfac—Endocellutions, "Legacy Needles are designed to pull a Small Aspirate From a Single Location," downloaded from www.marrowcellutions.com on Oct. 7, 2015 (1 page).
Ranfac—Endocellutions, "Marrow Cellution™—Bone Marrow Harvesting Systems," downloaded from www.marrowcellutions.com on Oct. 7, 2015 (2 pages).
Ranfac—Endocellutions, Presentation, "Marrow Cellution," downloaded from www.marrowcellutions.com on Oct. 7, 2015 (12 pages).
Ranfac, Fact Sheet, "Marrow Cellution—Bone Marrow Aspiration and Stem Cell Harvesting Systems," downloaded from www.marrowcellutions.com on Dec. 23, 2015 (2 pages).
Scarpone, M. A. et al., "Marrow Cellution Bone Marrow Aspiration System and Related Concentrations of Stem and Progenitor Cells," downloaded from www.marrowcellutions.com on Dec. 23, 2015 (6 pages).
Snarecoil™ Biopsy Needles—Technology that reduces the Time and Trauma of Bone Marrow Biopsies, retrieved from www.ranfac.com/pdf/bonemarrow.pdf, Mar. 15, 2010, (4 pages).
International Search Report and Written Opinion, PCT/US2013/067358, mailed Feb. 21, 2014, entitled "Apparatus And Methods For Aspirating Tissue,".
International Preliminary Report on Patentability and Written Opinion, PCT/US2013/067358, entitled "Apparatus And Methods For Aspirating Tissue," Issued May 5, 2015.
International Search Report and Written Opinion for International Application No. PCT/US2015/011614; date of mailing Apr. 20, 2015; entitled "Bone Marrow Harvesting Needle Improvements.".
Notification of Transmittal of the International Search Report and the Written Opinion of the International Searching Authority, or the Declaration, "Apparatus And Methods For Aspirating And Separating Components Of Different Densities From A Physiological Fluid Containing Cells", date of mailing Aug. 18, 2011.
Notification Concerning Transmittal of International Preliminary Report on Patentability for International Application No. PCT/US2015/011614; date of mailing Jul. 28, 2016, "Bone Marrow Harvesting Needle Improvements,".
Notice of Allowance and Fees Due, U.S. Appl. No. 15/721,123, entitled "Bone Marrow Access Device," dated Oct. 4, 2019.
Notice of Allowance and Fees Due, U.S. Appl. No. 14/439,022, entitled "Bone Marrow Harvesting Needle Improvements," date of mailing Nov. 2, 2018.
U.S. Office Action for U.S. Appl. No. 14/439,022, entitled "Apparatus And Methods For Aspirating Tissue," dated Sep. 5, 2017.
U.S. Final Office Action for U.S. Appl. No. 14/439,022 dated May 2, 2018, entitled "Apparatus And Methods For Aspirating Tissue," 21 pages.
U.S. Office Action for U.S. Appl. No. 14/885,821, entitled "Bone Marrow Aspiration Device And Method," dated Sep. 11, 2017.
U.S. Office Action for U.S. Appl. No. 14/885,821, dated Apr. 5, 2019 entitled "Bone Marrow Aspiration Device And Method,".
U.S. Final Office Action for U.S. Appl. No. 14/885,821 dated Jun. 14, 2018, entitled "Bone Marrow Aspiration Device And Method," 21 pages.
U.S. Office Action for U.S. Appl. No. 15/721,123, dated Mar. 29, 2019, entitled "Bone Marrow Access Device,".

\* cited by examiner

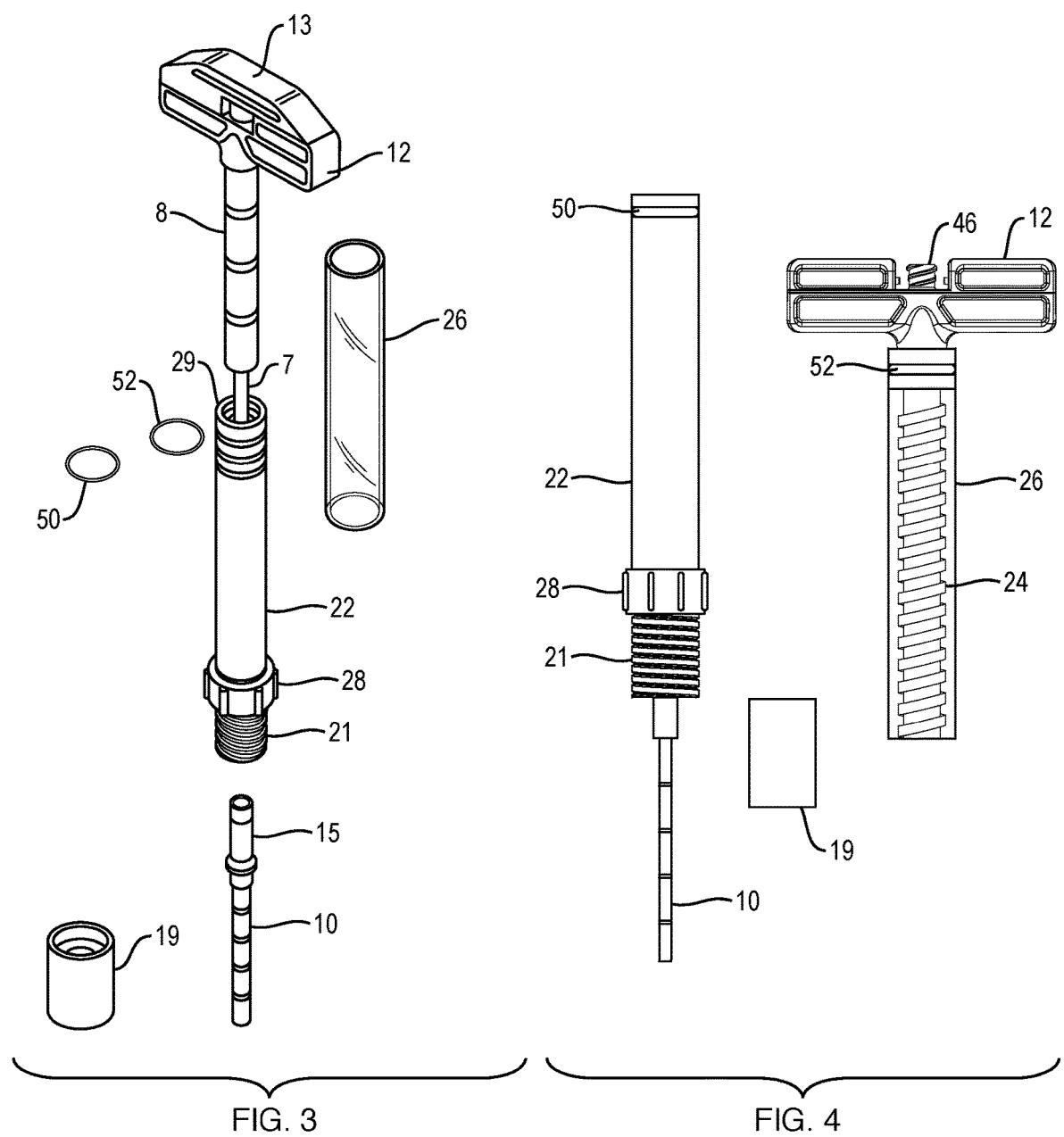

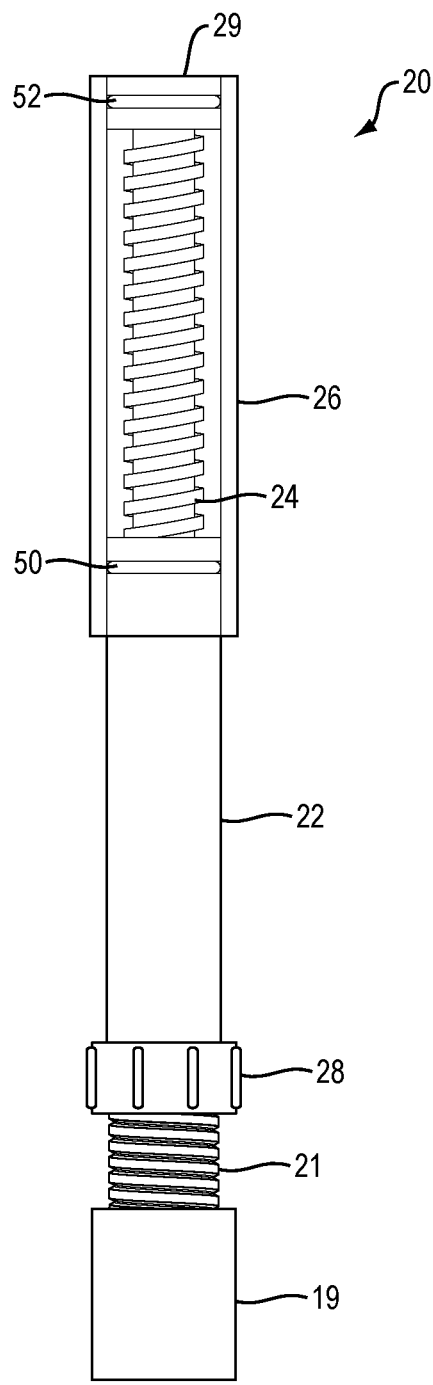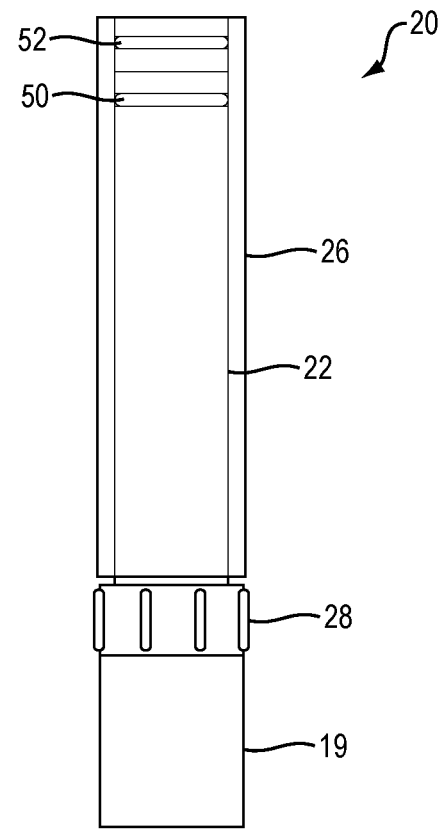
FIG. 5A
FIG. 5B

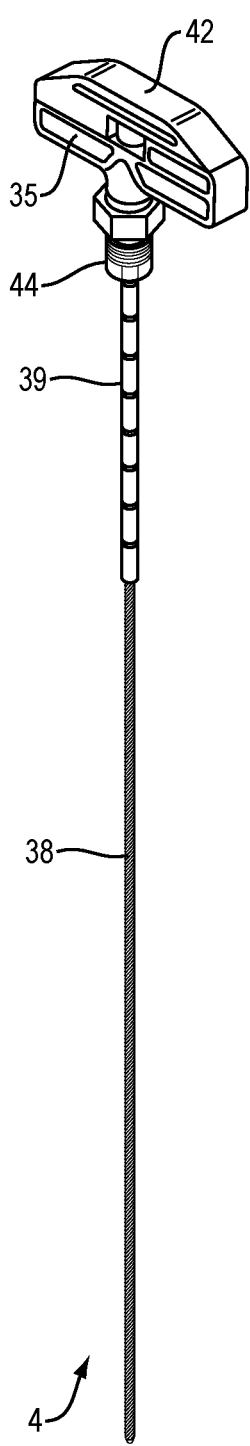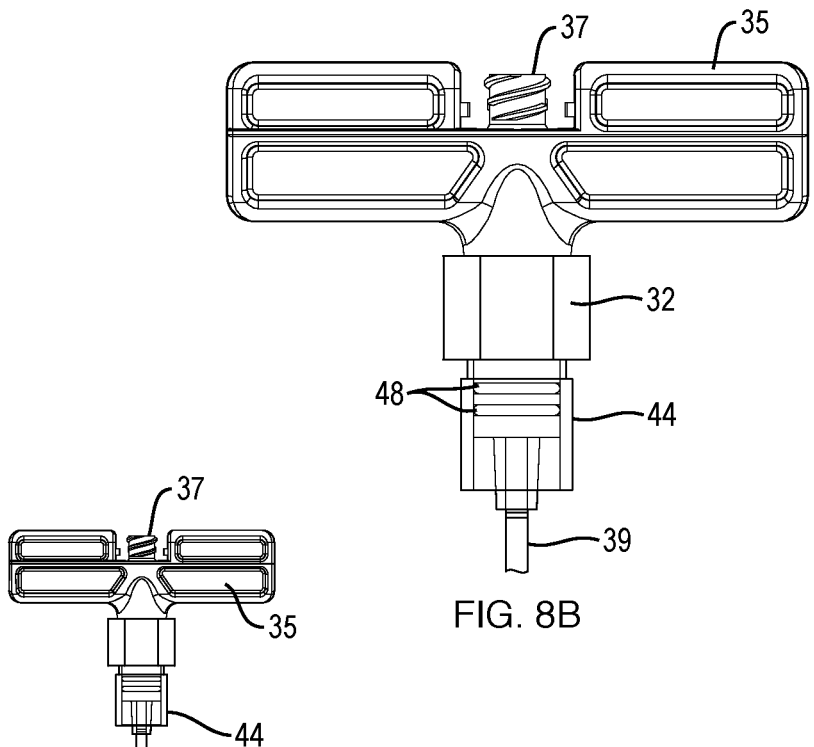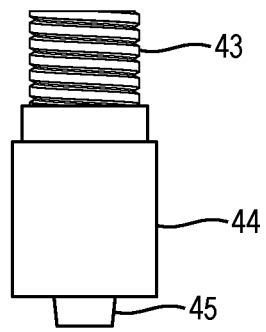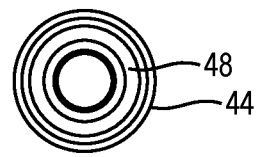
FIG. 7
FIG. 8A
FIG. 8B
FIG. 8C
FIG. 8D

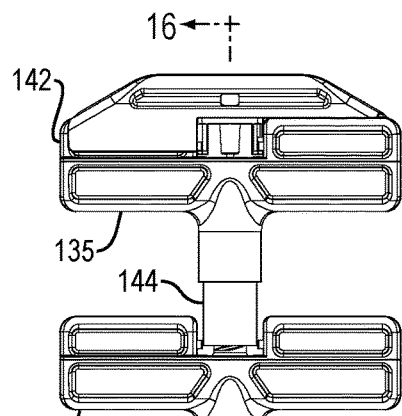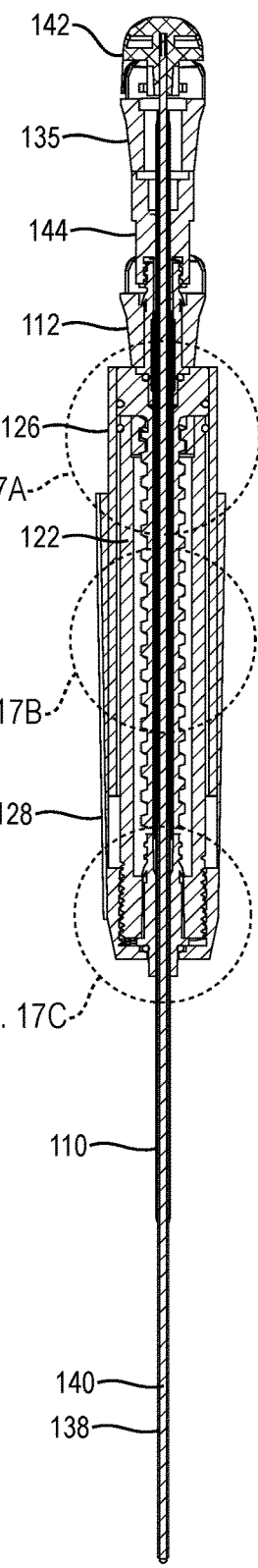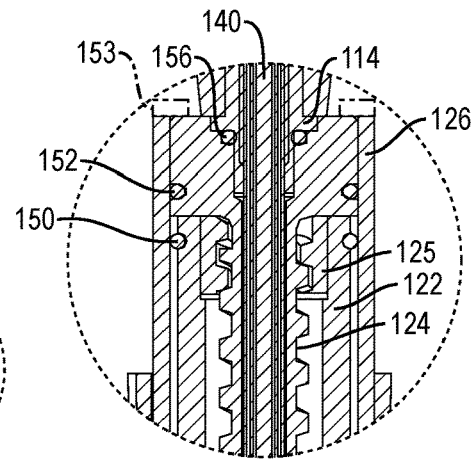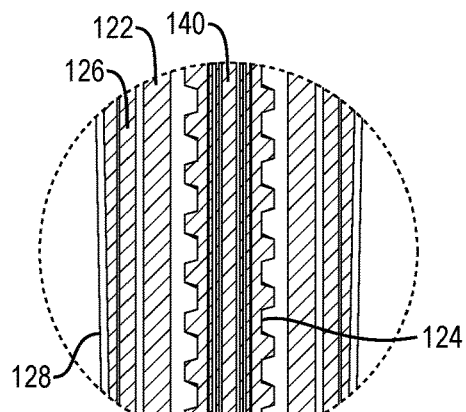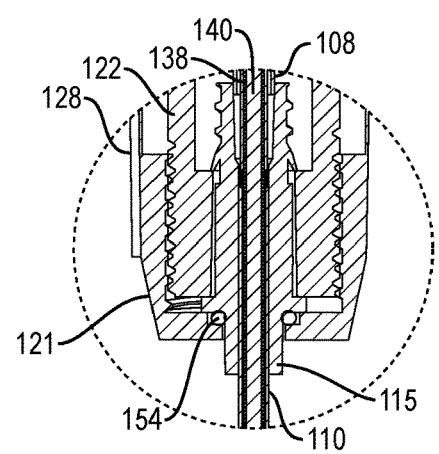
FIG. 15  FIG. 16

BONE MARROW HARVESTING NEEDLE IMPROVEMENTS

RELATED APPLICATIONS

This application is a continuation of U.S. application Ser. No. 16/732,630, filed Jan. 2, 2020, which is a divisional of U.S. application Ser. No. 15/110,520, filed Jan. 15, 2015, now U.S. Pat. No. 10,556,046, which is the U.S. National Stage of International Application No. PCT/US2015/011614, filed on Jan. 15, 2015, published in English, and claims the benefit of U.S. Provisional Application No. 61/927,614, filed on Jan. 15, 2014, 61/950,303, filed on Mar. 10, 2014, and 61/986,391, filed on Apr. 30, 2014. The entire teachings of the above applications are incorporated herein by reference.

BACKGROUND

Bone is made up of a hard outer core, known as cortical bone or cortical plate, and a soft spongy interior known as cancellous bone or trabecular bone, which includes a marrow filling in the porous space within the spongy bone (commonly referred to as bone marrow). The cortical plate is very hard and provides the rigid structure to the skeleton, which allows the skeleton to bear weight. Bone marrow is rich in capillary beds.

A traditional bone marrow aspiration needle is commonly used to access marrow from the hip or iliac bone. The traditional aspiration needle includes an aspiration cannula (also referred to as a cannulated trocar) and a removable stylet that extends through the cannula and has a sharp pointed tip. Because the traditional aspiration needle is stiff, the needle can only advance linearly within the marrow space. Once the needle is through the cortical plate, the cannula only has access to whatever marrow is directly ahead of the cannula tip, but cannot bend or access marrow to the sides of the cannula. Thus, clinicians often need to perform multiple punctures in order to gain larger volumes of aspirate from a more diverse cross section of the marrow space. Since the hip bone is long and thin, once the traditional aspiration needle has penetrated cortical bone, the sharp and stiff instrument has the potential to penetrate through the other side of the cortical bone, resulting in significant trauma. Consequently, it is important for the surgeon to have a proper angle and skilled technique to ensure a safe aspiration. Since the iliac crest curves from the front to the back of the patient, the best angle of entry is from the back. Since the stylet is made of a stiff material, once inside the spongy bone, the needle assembly can only go straight, thus requiring multiple punctures to obtain the required volume of aspirate.

A traditional marrow aspiration needle is meant to access bone marrow from larger cavities and is not ideally suited to drawing marrow from the smaller confines such as the vertebral body of the spine. Because of the sharpness and stiffness of a traditional aspiration needle, using such an instrument in the small curved marrow space of a vertebral body would greatly increase the likelihood of introducing trauma. Less invasive and safer methods to access the marrow tissue of the vertebral body are needed in an effort to support the emerging field of orthobiologics. One fast growing area of this field combines marrow aspirate with synthetic matrix material in order to facilitate instrumented assisted spinal fusion.

SUMMARY

A bone marrow aspiration device includes an introducer needle assembly and an aspiration needle assembly. The introducer needle assembly includes an introducer cannula having a proximal end and a distal end, each end including an opening. The introducer needle assembly further includes a screw assembly coupled to the introducer cannula. The screw assembly includes a threaded tube and a lead screw receivable in the threaded tube. An outer cover is disposed around and in sealing engagement with the threaded tube and the lead screw. The aspiration needle assembly is receivable in the introducer cannula and includes an aspiration cannula, the aspiration cannula having a proximal end and a distal end and including a distal flexible portion that extends along a length of the aspiration cannula. The aspiration cannula forms a channel for aspirating bone marrow. A length of the aspiration cannula that extends beyond the distal end of the introducer cannula is adjustable by advancing the lead screw into the threaded tube or reversing the lead screw out of the threaded tube.

The flexible portion of the aspiration cannula can include a wire wound tube. In an embodiment, the wire wound tube has a winding in one direction, and the screw assembly is configured to allow the aspiration cannula to be withdrawn from the bone marrow by turning the aspiration cannula in a direction opposite to the direction of the winding, whereby the wire wound tube is tightened as the aspiration cannula is turned and withdrawn.

The introducer cannula can include an upper cannula and a lower cannula in axial alignment with the upper cannula, the upper cannula being coupled to the lead screw, the lower cannula being coupled to the threaded tube of the screw assembly. In an embodiment, the lower cannula extends from a needle hub coupled to the threaded tube, the upper cannula butting against the needle hub when the screw assembly is in a collapsed state.

The aspiration needle assembly can include a blunt stylet receivable in the aspiration cannula. In an embodiment, the distal end of the aspiration cannula includes an opening and the blunt stylet is configured to extend through and close the opening.

The aspiration needle assembly can include a connector to couple to the introducer needle in an air-tight manner. The aspiration needle assembly can further include an aspiration handle connected to the proximal end of the aspiration cannula. In an embodiment, the aspiration handle includes a port in fluid communication with the aspiration cannula for aspirating or injecting fluid or fluid containing cells, including bone marrow.

An introducer handle can be connected to the proximal end of the screw assembly. The lead screw of the screw assembly can be attached to the introducer handle. The outer cover can be an outer rigid tube that is attached to the lead screw, e.g., at a proximal end of the lead screw, and that rides along the threaded tube. In an embodiment, the lead screw is hollow and the introducer cannula extends through the hollow lead screw. The aspiration device can further include an O-ring between the threaded tube and the outer cover to form the sealing engagement. The screw assembly can include a finger grip that extends along a length of the threaded tube. In an embodiment, the finger grip is a sleeve that extends around the outer cover (e.g., outer tube) and the threaded tube.

The aspiration device can further include a removable introducer stylet having a proximal end and a distal end, the stylet extending through the introducer cannula, e.g., from the introducer handle, the distal end of the stylet extending beyond the distal end of the introducer cannula and including a sharp tip to penetrate bone. The aspiration needle assembly is receivable in the introducer cannula when the introducer stylet is removed from the introducer needle assembly.

A method for aspirating bone marrow includes inserting an aspiration needle assembly into bone marrow through an introducer cannula placed in a bone. The aspiration needle assembly includes an aspiration cannula, the aspiration cannula having a proximal end and a distal end and including a distal flexible portion that extends along a length of the aspiration cannula. The aspiration cannula forms a channel for aspirating bone marrow. The method further includes adjusting a length of the aspiration cannula that extends beyond a distal end of the introducer cannula using a screw assembly coupled to the introducer cannula, and aspirating bone marrow through the channel. The screw assembly includes a threaded tube and a lead screw receivable in the threaded tube, while an outer cover is disposed around and in sealing engagement with the threaded tube and the lead screw.

Adjusting the length of the aspiration cannula that extends beyond the distal end of the introducer cannula can include advancing the lead screw into the threaded tube or reversing the lead screw out of the threaded tube.

Inserting the aspiration needle assembly into bone marrow can include flexing or bending the assembled aspiration cannula and blunt stylet against cortical bone.

The method for aspirating bone marrow can further include removing the blunt stylet from the aspiration needle assembly, the aspiration cannula forming the channel for aspirating the bone marrow when the stylet is removed.

Aspirating bone marrow can include retracting the aspiration cannula from the bone. In an embodiment, retracting the aspiration cannula from the bone includes employing the screw assembly to shorten the length that the aspiration cannula extends beyond the distal end of the introducer cannula.

The method can further include, before inserting the aspiration needle assembly, penetrating cortical bone with an introducer needle assembly. The introducer needle assembly includes the introducer cannula having a proximal end and a distal end, each end including an opening, an introducer stylet having a proximal end and a distal end, the stylet extending through the introducer cannula, the distal end of the stylet extending beyond the distal end of the introducer cannula and including a sharp tip to penetrate bone. The method further includes removing the introducer stylet before inserting the aspiration needle assembly.

The method can further include advancing the introducer needle assembly into the bone to a selected depth before removing the introducer stylet. In the method, bone marrow can be aspirated while the length of the aspiration cannula that extends beyond the distal end of the introducer cannula is adjusted.

In an embodiment, the sealing engagement between the outer cover (e.g., outer tube) and the threaded tube includes a dynamic seal and the sealing engagement between the outer cover (e.g., outer tube) and the lead screw includes a static seal.

A bone marrow aspiration device includes an introducer needle assembly that includes an introducer cannula having a proximal end and a distal end, each end including an opening. The introducer needle assembly further includes a screw assembly coupled to the introducer cannula, the screw assembly including a threaded tube and a lead screw receivable in the threaded tube, and a dynamic O-ring seal between the lead screw and the threaded tube at a non-threaded portion of the threaded tube. The device further includes an aspiration needle assembly receivable in the introducer cannula. The aspiration needle assembly includes an aspiration cannula having a proximal end and a distal end and including a flexible portion that extends from the distal end along a length of the aspiration cannula, the aspiration cannula forming a channel for aspirating bone marrow. A length of the aspiration cannula that extends beyond the distal end of the introducer cannula can be adjusted by advancing the lead screw into the threaded tube or reversing the lead screw out of the threaded tube.

In an embodiment, the introducer needle assembly includes an outer tube disposed around and in sealing engagement with the threaded tube and the lead screw, the dynamic O-ring seal being formed between the outer tube and the threaded tube. The introducer needle assembly can further include an introducer handle coupled to a proximal end of the screw assembly.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3 and 4 are exploded and side views, respectively, of components of the introducer needle assembly of FIG. 1.

FIG. 5A is a side view of the screw assembly of the introducer needle assembly in an extended state.

FIG. 5B is a side view of the screw assembly of the introducer needle assembly in a collapsed state.

FIG. 7 is a perspective view of a fully assembled flexible needle.

FIGS. 8A to 8D illustrate components of the flexible needle.

FIGS. 14 and 15 are a front and back views, respectively, of the aspiration device of FIG. 12.

FIG. 16 is a sectional view of the aspiration device of FIG. 15.

FIGS. 17A, 17B, and 17C illustrate details of the sectional view of FIG. 16.

DETAILED DESCRIPTION OF THE INVENTION

A description of example embodiments of the invention follows.

Bone marrow aspiration devices including an introducer cannula and a flexible aspiration cannula are described in International Application No. PCT/US2010/036696, filed on May 28, 2010 and published on Dec. 2, 2010 as WO 2010/138895 A2, and International as WO 2014/070804, the teachings of which are incorporated herein by reference in their entireties.

The following describes an improvement to a double cannula aspiration device that is used to harvest bone marrow and that was previously described in WO 2010/138895. It was observed that while the trabecular bone is not as hard as the cortical bone, it is often too hard to advance the aspiration needle by hand. In fact, a hammer is often required to drive the second needle through the trabecular bone space. Advancing the needle by force such that it bends can lead to problems such as the needle becoming lodged (stuck) inside the patient. Therefore, an improvement is needed to allow the second, flexible needle to advance through the trabecular bone and then apply sufficient force to allow the surgeon to retrieve the needle once advanced.

The industry standard is to measure needle diameters by gauge, not millimeters or inches; the larger the gauge, the smaller the needle diameter. Thus, an 8-gauge needle has a larger diameter than an 11-gauge needle.

Figure 1:
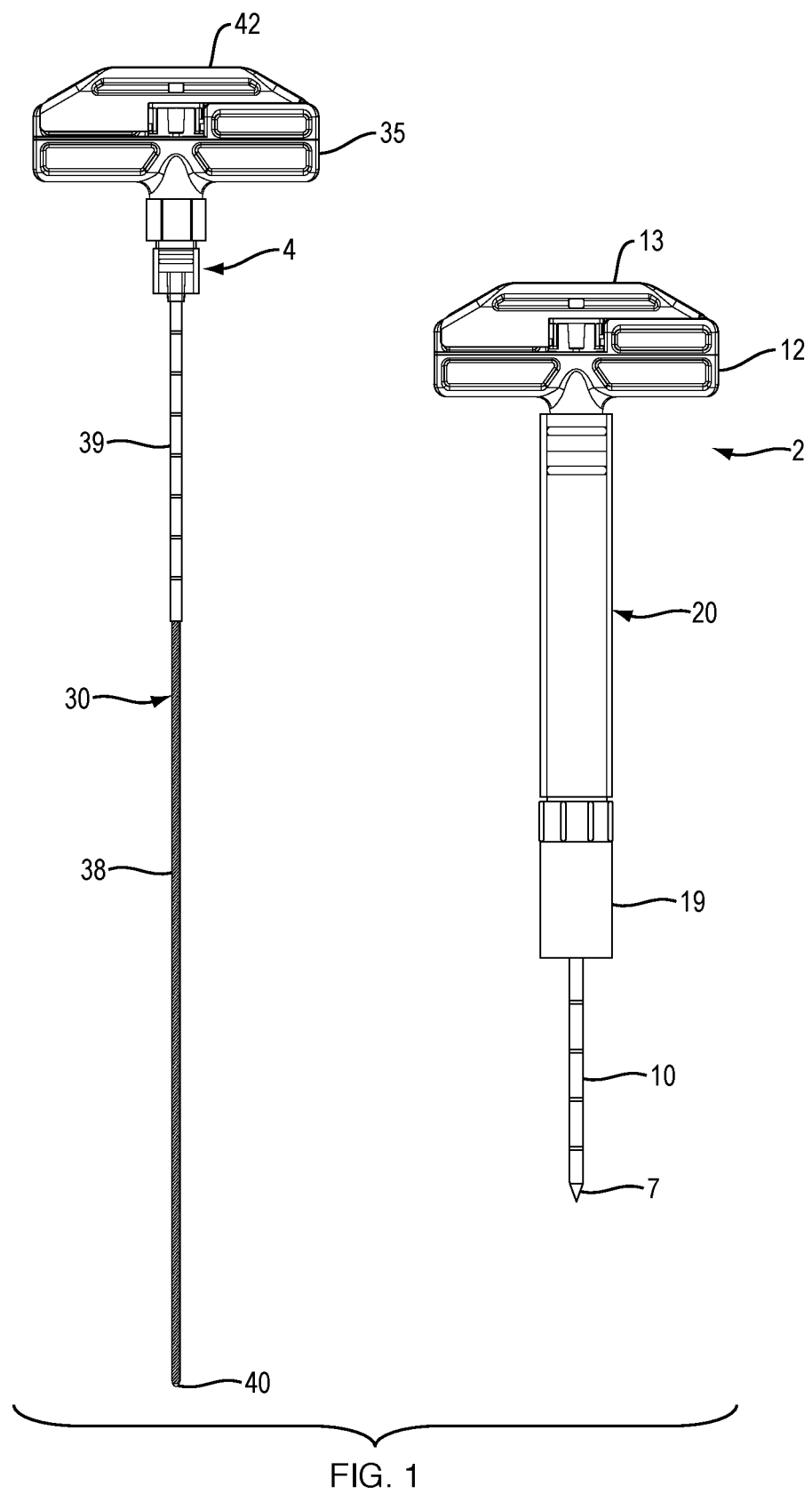
FIG. 1 illustrates an example aspiration device including an introducer needle assembly and flexible aspiration needle assembly.
Figure 2:
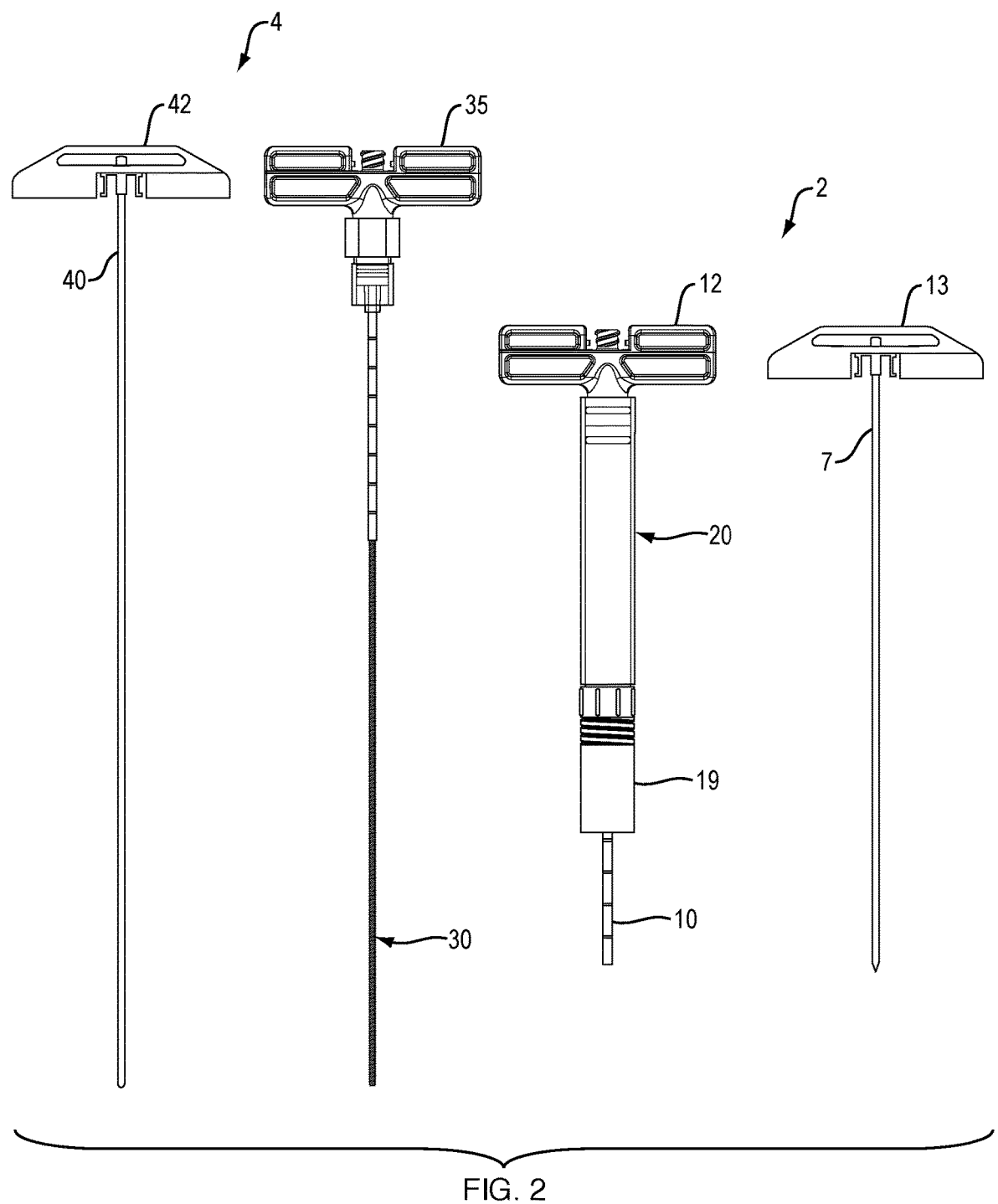
FIG. 2 illustrates the introducer needle assembly and flexible aspiration needle assembly of FIG. 1 with respective stylets removed.

FIG. 1 illustrates an example aspiration device including an introducer needle assembly and flexible aspiration needle assembly. FIG. 2 illustrates the introducer needle assembly and flexible aspiration needle assembly of FIG. 1 partially disassembled.

As illustrated in FIGS. 1 and 2, an example aspiration device includes a bone marrow introducer needle assembly 2 (also referred to herein as "introducer needle") and a flexible aspiration needle assembly 4 (also referred to herein as "flexible needle" or "flexie needle" or "flex needle"). In the example shown, the introducer needle assembly 2 includes an 11-gauge bone marrow aspiration cannula 10 attached to a novel upper needle assembly, described in more detail below, with a removable sharp stylet 7, a screw mechanism 20, and an optional depth guide 19. The flexible needle assembly 4 includes a 13-gauge bone marrow aspiration cannula 30 with blunt stylet 40. A portion of the aspiration cannula 30 is flexible. The entire length of the cannula 30 may be formed from a wire wound tube or only a portion of the cannula may be. As shown, the 13-gauge aspiration cannula 30 is made from a wire wound tube (coil spring) 38 (FIG. 9) and has an outer cannula jacket 39 covering part of the upper end of the wired wound tube near handle 35 of the flexible needle assembly (see also FIGS. 7-9).

FIG. 2 illustrates the introducer needle 2 and flexible aspiration needle 4 of FIG. 1 with stylets 40 and 7 removed from respective cannulae 30 and 10. The introducer needle 2 is shorter than the relatively long flexie needle 4 that has the wire wound tube (coil spring). The long flexie needle 4 is designed to fit through the introducer needle 2 and extend beyond the distal end of the introducer needle. The portion of the introducer needle 2 that enters the body is an 11-gauge cannula 10 that is attached to the bottom of screw mechanism 20 positioned distal to handle 12. The introducer needle includes a sharp stylet 7 that fits through the handle 12 and protrudes slightly from the distal end of the 11-gauge cannula 10 located at the lower end of the introducer needle 2. When stylet 7 is fully inserted into needle 2, stylet handle 13 couples with introducer handle 12 (see FIGS. 1 and 6). The combination of the lower cannula 10 and stylet 7 of the introducer needle 2 allows the introducer needle to penetrate the hard outer cortical bone. The lower cannula 10 is attached to the lower end of a female tube 22 (FIGS. 3-4) of screw mechanism 20 and is approximately 2 inches in length. In this example, adjustable depth guard 19, screwed to the bottom of female tube 22, can be advanced to cover a portion of the 11-gauge cannula 10 to control the depth of entry of cannula 10 into tissue, e.g, into bone. The stylet 7 fits through handle 12 which has an 8-gauge upper cannula 8 (FIG. 3) attached to it. The 8-gauge upper cannula 8 is covered by a lead screw 24 that fits into threaded (female) tube 22. Female tube 22 is covered by a clear outer tube 26 and an O-ring 50 is positioned between tubes 22 and 26 as illustrated in FIG. 2, and further illustrated in FIGS. 3-4. The O-ring provides a dynamic seal between outer tube 26 and threaded tube 22 to keep the threads of the screw mechanism 20 air tight as the user moves the screw mechanism.

The following describes elements of the introducer needle 2 and how these elements fit together. FIG. 3 is an exploded view of the elements of the introducer needle 2 of FIG. 1. FIG. 4 is a side view of the introducer needle 2 partially disassembled and with the stylet 7 removed, illustrating components of screw assembly 20. The 8-gauge cannula 8 extends from handle 12 of introducer needle 2 and fits through the hollow center of the lead screw 24, of which only head 29 is shown in FIG. 3. The lead screw 24 mates into the female tube 22 which has a corresponding thread to the lead screw. The clear outer tube 26 is rigid and fits over the female (threaded) tube 22. At least one O-ring 50 on the female tube 22 is compressed by the outer tube 26 to keep air from moving past the O-ring and through the threads. The 11-gauge lower cannula 10 and hub 15 fit into the bottom of female tube 22. The stylet 7 fits into the 11-gauge needle 10 and hub 15 and the 8-gauge upper cannula 8 attached to handle 12. The stylet 7 is long enough to pass through both the 8-gauge upper cannula 8 and handle 12 and the 11-gauge lower cannula 10 and hub 15. In the example shown, cannula 8 is a stainless steel cannula, handle 12 a molded plastic handle, cannula 10 a stainless steel cannula, and hub 15 a molded plastic hub. The stylet 7 is stainless steel with a molded plastic handle 13 that mates with handle 12 when the stylet is inserted through handle 12, cannula 8, hub 15 and cannula 10.

FIGS. 5A-5B are side views of the screw assembly 20 of the introducer needle 2 without the handle, cannula and stylet. FIG. 5A shows the lead screw 24 that advances into the female tube 22 which is covered by a clear outer tube 26 that slides over an O-ring 50 that is on the outside of the upper female tube 22. At the bottom of tube 22, below finger grip 28, is optional depth guide 19 that can be screwed onto threads 21 of tube 22. The lead screw 24 and female tube 22 have a through hole (not shown) such that the various sized cannula and stylets can fit through. The internal shape of the upper end 29 of the lead screw is shaped so that the handle 12 of the introducer needle fits securely. The internal shape of the lower end of the female tube 22 is shaped so that the 11-gauge needle hub 15 fits securely. The O-ring 50 on the upper portion of the female (threaded) tube 22 keeps air from leaking into the center of the introducer needle 2 (and into the aspiration cannula 4 when inserted into needle 2) through the threads of the screw assembly 20 as the lead screw 24 is advanced or retrieved. This is a novel way to keep the apparatus air tight around multiple parts as they move. Other static joints (i.e. a seam that does not involve one part moving through or over another; a static seal) can be kept airtight by a number of methods such as tight fit with glue, ultrasonic welding, tapered press fit, O-ring, or combinations of the above. For example, the static joint between the top of the clear outer tube 26 and the lead screw 24 can be kept air tight by using a second O-ring 52.

In FIG. 5B, the screw assembly 20 is illustrated in a collapsed state with threaded parts, e.g., lead screw 24 and guide 19 on threads 21 of tube 22, advanced as far as possible. When the threaded parts are advanced as shown, the introducer needle 2 has its shortest profile.

Figure 6:
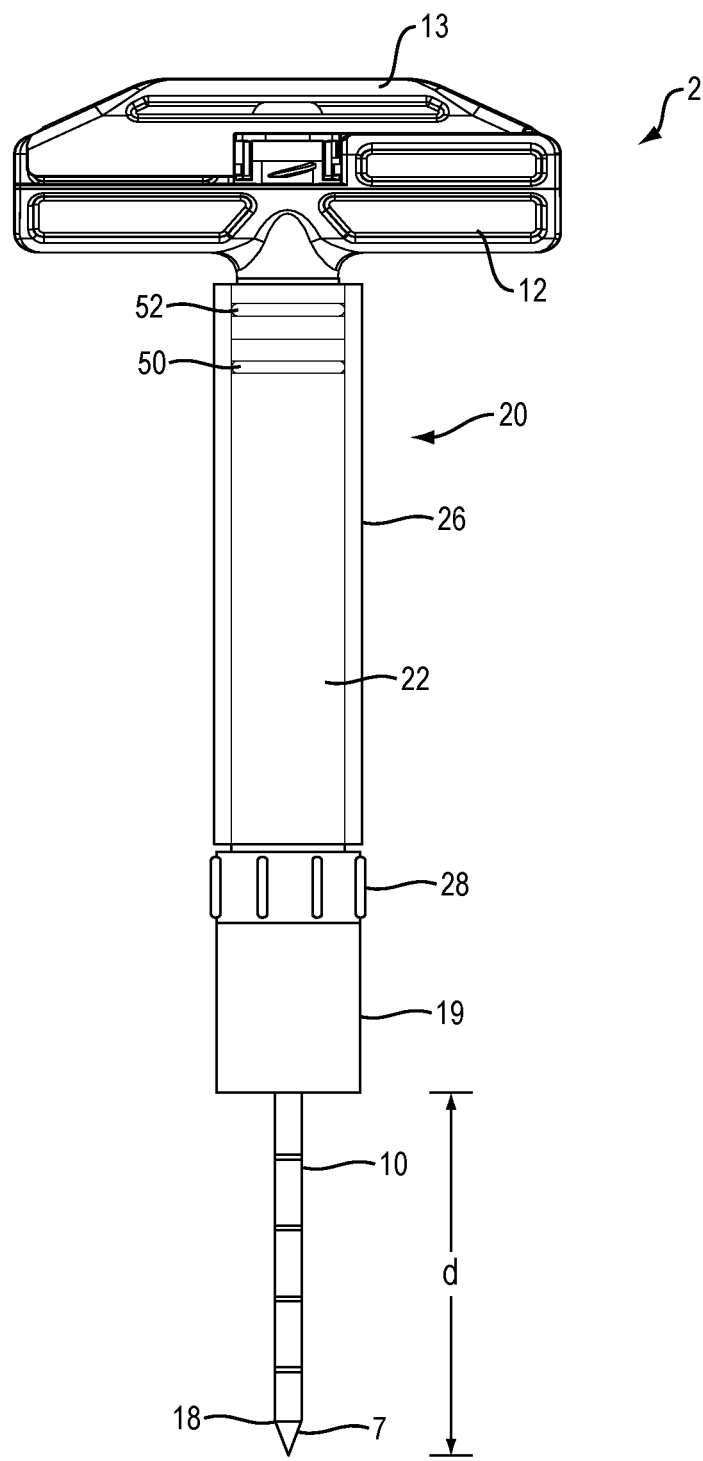
FIG. 6 illustrates a fully assembled introducer needle.

FIG. 6 is a view of the introducer needle 2 fully assembled with the needle handle 12, cannula 10, and stylet 7, whose handle 13 is interlocked with handle 12. The threaded parts, including lead screw 24 (not visible as inside tube 22 and outer tube 26) and guide 19, are collapsed giving the needle 2 its shortest profile. As shown, the sharp tip of stylet 7 protrudes slightly from distal end 18 of cannula 10. The distal end of cannula 10 has a sharpened cannula leading edge. The combination of the sharp stylet 13 and leading edge of cannula 10 is useful to penetrate the outer cortical bone. The adjustable depth guide 19 on the bottom of the female tube 22 under the finger grips 28 allows the user to adjust the depth to which the needle 2, e.g., cannula 10 and stylet 7, will advance into the bone space. The distance d between the distal end of depth guide 19 and the distal end of stylet 7 represents the furthest distance that the introducer needle can penetrate before being stopped by the depth guide.

FIG. 7 illustrates a fully assembled flexible needle. The flexie needle 4 is longer than the introducer needle 2 (see FIG. 2) and it is made from a wire wound coil spring 38. Stylet 40, of which only handle 42 is visible in FIG. 7, extends through the length of needle 4. The long flexie needle is 13 gauge and is designed to fit through the introducer needle 2. As described above with reference to FIG. 3, the cannula of the introducer needle 2 includes an 11-gauge lower cannula 10 and an 8-gauge upper cannula 8, such that the cannula 30 of the flexie needle easily fits through the cannula of the introducer needle. Because the wire wound tube (spring coil) 38 and stylet 40 (FIG. 2) of the flexie needle 4 are sufficiently flexible and the stylet 40 has a blunt rounded end, this needle can bend around the inner bone surface without penetrating the cortical plate. The flexie needle 4 is long enough so that it can exit the distal end of the introducer needle 2 and travel an additional distance, e.g., 3 inches, further into the bone (see also FIGS. 10A-10C and associated description).

FIGS. 8A to 8D further illustrate components of the flexible needle. As shown in FIG. 8A, stylet handle 42 has been disconnected from handle 35 of the flexible needle and stylet 40 has been removed, thereby exposing connector 37 at handle 35 for connecting a syringe for aspiration of bone marrow. Connector 37 of the aspiration handle can include a port in fluid communication with the aspiration cannula for aspirating or injecting fluid or fluid containing cells, including bone marrow. As shown, the upper end of the flexie needle 4 includes a solid 11-gauge stainless steel jacket 39 around an upper part of needle, e.g., around the upper 3 inches. Under the handle 35 of the flexie needle is a standard luer connector 44, such as a tapered luer fitting. This connector 44 can connect the flexie needle to the luer hub 46 of the introducer needle 2 once the introducer stylet 7 has been removed. In the example shown, the luer connector 44 is screwed into nut 32 that is glued to handle 35. Other means for sealingly attaching connector 44 to handle 35 are contemplated. Further, connector 44 may be integrally formed with handle 35. FIGS. 8C and 8D are side and top views, respectively, of an example connector 44. As illustrated in FIG. 8C, connector 44 can include a threaded end 43 to screw into nut 32 and a tapered luer fitting 45 to connect to the introducer needle. As illustrated in FIGS. 8B and 8D, connector 44 can include one or more O-rings 48 that fit inside the luer connector. The O-ring(s) 48 in combination with the tapered luer fitting 45 provide for an air-tight connection of the aspiration needle 4 to the introducer needle 2.

Figure 9:
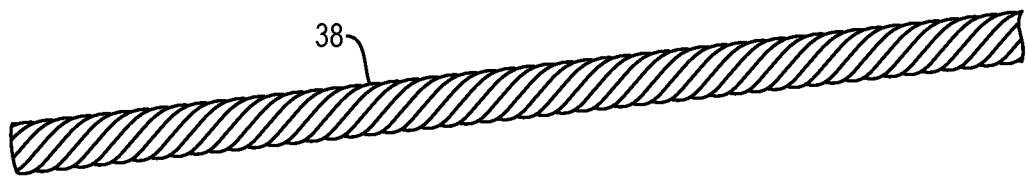
FIG. 9 is a close-up view of a coil spring of a flexible portion of the aspiration cannula.

FIG. 9 is a close-up view of a coil spring 38 of a flexible portion of the aspiration cannula 30. The wire wound tube 38 can have a winding in one direction, and the screw assembly 20 of the introducer needle 2 can be configured to allow the aspiration cannula 30 to be withdrawn from the bone marrow by turning the aspiration cannula in a direction opposite to the direction of the winding. In this way, the wire wound tube 38 is tightened as the aspiration cannula is turned and withdrawn. The wire can be stainless steel, for example wire part 305V steel, and can be wound in a left hand lay.

Figures 10A, 10B, 10C:
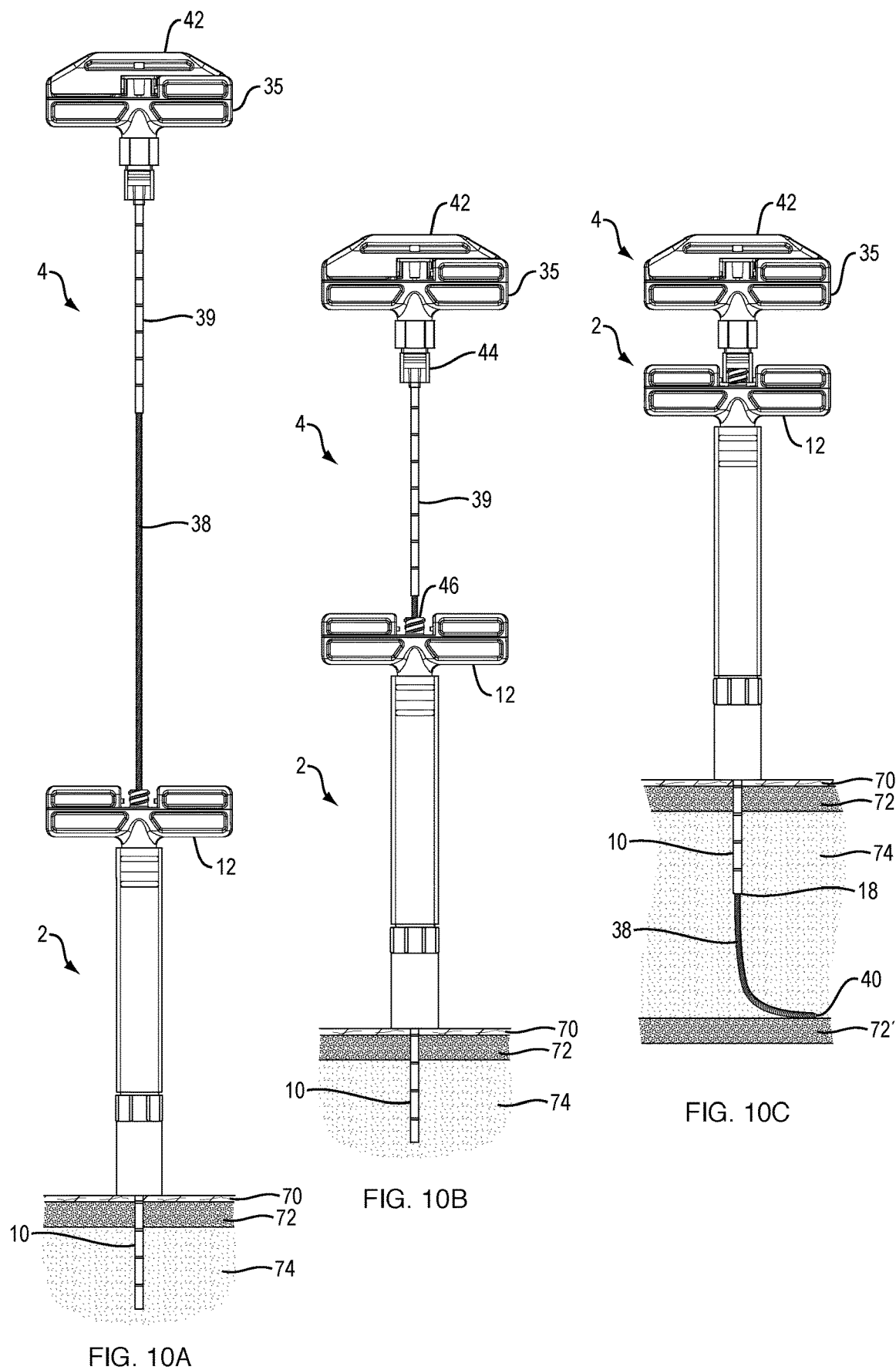
FIGS. 10A to 10C illustrate the flexible needle being advanced through the introducer needle.

A user of an aspiration device described herein may first insert the assembled introducer needle 2 (FIG. 6) into the cortical bone in a manner similar to a traditional JAMSHIDI bone marrow needle. The introducer needle may be advanced into the bone to a selected depth using the optional depth guide 19 described in reference to FIGS. 3-6. After the sharp stylet 7 and cannula 10 have passed the cortical plate and the tip of the needle 2 is in the marrow space, the stylet 7 is removed. FIGS. 2 and 10A illustrates the introducer needle 2 with the introducer stylet 7 removed. At this point, the user may choose to connect a syringe or other receptacle to the luer connector 46 (FIG. 4) of the introducer handle 12 and aspirate tissue from the marrow space. Because the screw assembly 20 of the introducer needle 2 is fully collapsed, as for example described above in reference to FIGS. 5B and 6, the upper cannula 8 is coupled to the lower cannula 10 via the lower needle hub 15 (FIG. 3), thereby establishing a channel for aspiration.

Once the user is confident that the introducer needle 2 has penetrated the outer cortical plate and the introducer stylet 7 has been removed, the user inserts the flexie needle 4 through the introducer needle 2 to go deeper into the marrow space.

FIGS. 10A to 10C illustrate the flexible needle 4 being advanced through the introducer needle 2 inserted in to bone. As shown in FIG. 10A, the introducer cannula 10 has penetrated skin 70 and cortical bone 72 and extends into bone marrow 74. The flexible needle 4 is advanced with stylet 40 (FIG. 2) in place and stylet handle 42 coupled to handle 35 of the flexible needle. When advancing the flexible needle, the user typically will hit stiff trabecular bone at the very distal end of the introducer needle 2. Trabecular bone is hard, but not as hard as cortical bone. To keep the upper portion of the flexie needle 2 from bending as the user applies force, the upper part of the flexie needle, which is equal to the distance the flexie needle can advance into the body, is wrapped in a stiffening jacket 39, e.g., a stainless steel 11-gauge cannula. This will support the exposed part of the flexie needle, e.g., wire wound tube 38, on the upper end. FIG. 10B shows the flexi needle 4 advanced until it has reached the distal end of introducer needle 2 (i.e. distal end of cannula 10). At this point, any portion of the wire wound tube 38 that is not under jacket 39 is entirely inside the introducer needle 2. The user can now further advance the aspiration needle 4 into bone marrow 74 beyond the distal end of introducer needle 2. As shown in FIG. 10C, the flexible needle 4 has been advanced such that its distal portion, i.e., the distal portion of wire wound tube 38, extends beyond the distal end 18 of cannula 10. In one example, the wire wound tube 38 extends about 3 inches beyond distal end 18. As shown, wire wound tube 38 of the aspiration cannula and stylet 40 have been advanced hitting cortical bone 72' on the other side of the bone and flex or bend against the cortical bone. Once the flexie needle 4 has been advanced a sufficient distance, the luer connection 44 on the bottom of the flexie needle handle 35 attached to the nut is connected to the luer connection 46 on the handle 12 of the introducer handle. The user can then uncouple stylet handle 42 from handle 35 of the aspiration needle and remove the flexible stylet 40. Next, the user can connect a syringe to the luer connector of handle 35 and begin to aspirate through the aspiration channel of aspiration needle 4.

Figure 11:
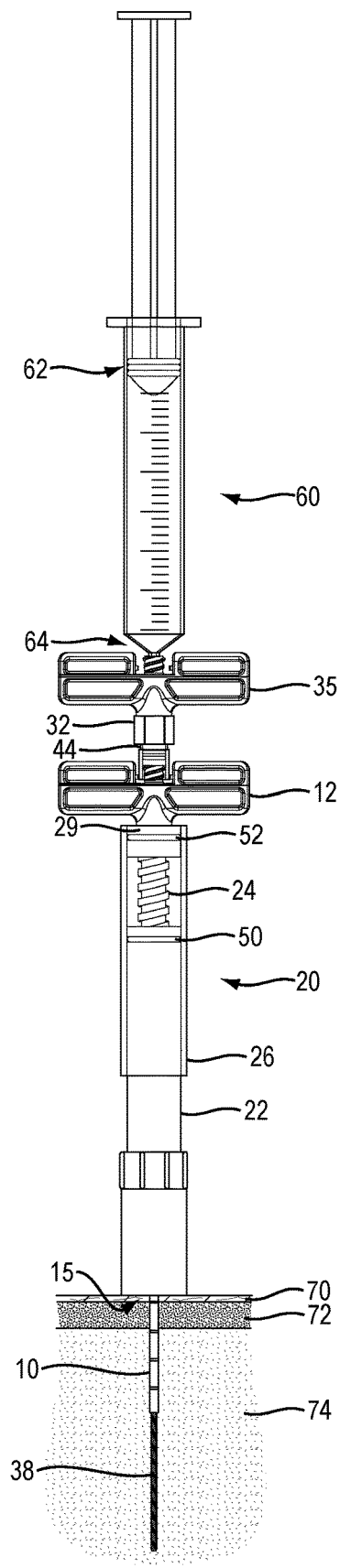
FIG. 11 illustrates a syringe attached to the flexible needle for aspiration of bone marrow as the flexible needle is being retrieved through the introducer needle using the screw assembly.

FIG. 11 illustrates the flexible needle being retrieved from bone marrow through the introducer needle using the screw assembly 20. The user has attached a syringe 60 to the luer connector 37 of the handle of the aspiration needle 4 and aspirates bone marrow 74 as the lead screw 24 of the screw mechanism 20 is engaged. Engaging the lead screw of screw mechanism 20 in one direction pulls the wire wound tube 38 back through the introducer cannula 10. The force of the screw mechanism 20 will reduce or eliminate the risk that the flexie needle 4 remains stuck inside the marrow space of a patient. In addition, the screw mechanism allows for measured withdrawal of the aspirate. Bone marrow 74 can be aspirated while the length of the flexible portion, e.g., wire wound tube 38, of the aspiration cannula 30 that extends beyond the distal end of the introducer cannula 10 is adjusted. For example, a user can aspirate while advancing the wire wound tube 38 into bone marrow 74 or retracting the wire wound tube from the bone marrow. The assembly shown in FIG. 11 includes at least the following air-tight joints: joint of plunger to barrel 62 of syringe 60, syringe connector 64 to luer connector 37 of aspiration needle 4, luer connection to nut 32 of handle 35, luer connection 44 to handle 12 of introducer needle 2, O-ring 52 at connection of lead screw head 29 to handle 12, O-ring 50 at connection of outer tube 26 to threaded tube 22, and connection of lower needle hub 15 to threaded tube 22. With all joints air tight, the wire wound tube 38 will not leak air. Because the distal end of wire wound tube 38 is in the body of the patient, vacuum pressure from syringe 60 will only pull tissue, e.g., bone marrow, from the body of the patient, not air.

FIGS. 12-17C illustrate an aspiration device according to another example embodiment of the invention.

Figure 12:
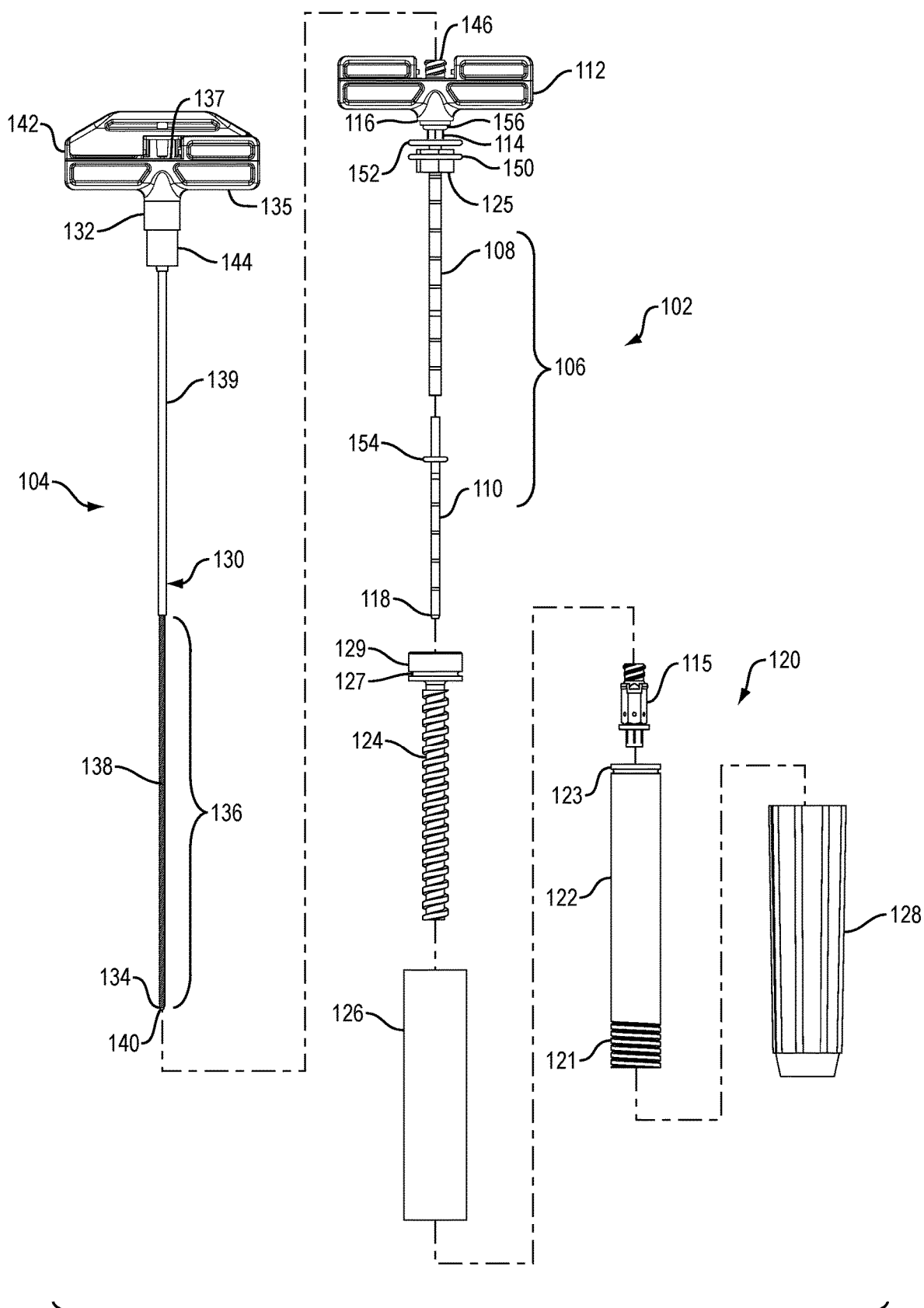
FIG. 12 is an exploded view of an aspiration device according to another example embodiment of the invention.

As shown in FIG. 12, the bone marrow aspiration device includes an introducer needle 102 and an aspiration needle 104. The introducer needle 102 includes an introducer cannula 106 having a proximal end 116 and a distal end 118, each end including an opening. The introducer needle further includes an introducer handle 112 connected to the proximal end 116 of the introducer cannula. A screw assembly 120 is coupled to the introducer handle 112. The screw assembly 120 includes a threaded tube 122 and a lead screw 124 receivable in the threaded tube. An outer tube 126 is disposed around and in sealing engagement with the threaded tube 122 and lead screw 124. In this example, the threaded tube 122 includes a nut 125 with a thread configured to engage the corresponding thread of lead screw 124. The aspiration needle 104 is receivable in the introducer cannula 106 and includes an aspiration cannula 130 having a proximal end 132 and a distal end 134. Aspiration cannula 130 includes a flexible portion 136 that extends from the distal end 134 along a length of the aspiration cannula. The aspiration cannula forms a channel for aspirating bone marrow. A length L (FIG. 14) of the aspiration cannula 130 that extends beyond the distal end 118 of the introducer cannula is adjustable by advancing the lead screw 124 into the threaded tube 122 or reversing the lead screw out of the threaded tube.

The flexible portion 136 of the aspiration cannula includes a wire wound tube 138. The wire wound tube 138 can have a winding in one direction, and the screw assembly 120 can be configured to allow the aspiration cannula 130 to be withdrawn from the bone marrow by turning the aspiration cannula in a direction opposite to the direction of the winding, whereby the wire wound tube 138 is tightened as the aspiration cannula is turned and withdrawn. The aspiration cannula 130 includes a relatively stiff portion 139. In the example shown, the stiff portion is a cannula that extends from the handle of the aspiration needle 104 and that is connected at its distal end to the wire wound tube 138. As described above in reference to FIGS. 1 and 7, the stiff portion can be a stainless steel sleeve (e.g., cannula jacket 39) disposed around a portion of the wire wound tube.

As illustrated in FIG. 12, the introducer cannula 106 includes an upper cannula 108 and a lower cannula 110 in axial alignment with the upper cannula. The upper cannula 108 is connected to introducer handle 112 via an upper needle hub 114. The lower cannula 110 is coupled to threaded tube 122 of the screw assembly 120. The lower cannula 110 extends from a lower needle hub 115 coupled to the threaded tube 122. The upper cannula 108 butts against the lower needle hub 115 when the screw assembly is in a collapsed state, as shown in FIG. 16 and in further detail in FIG. 17C.

Figure 13:
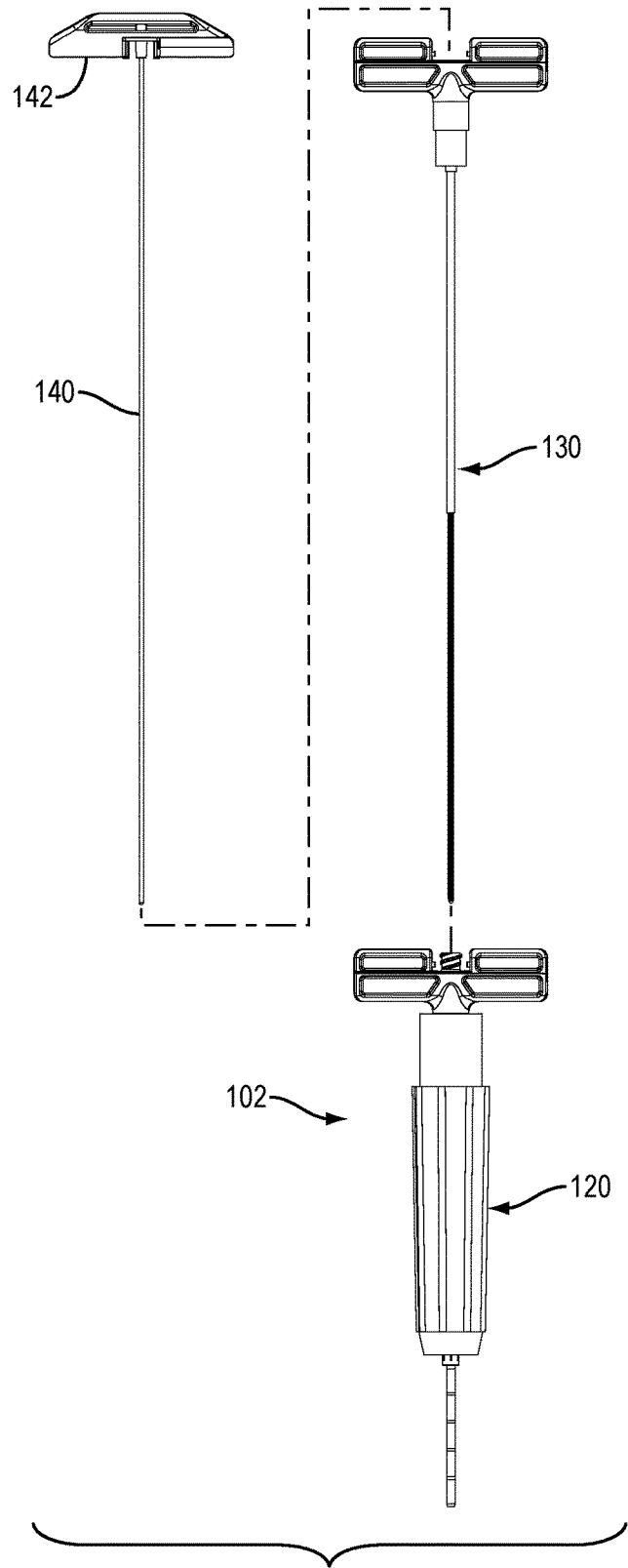
FIG. 13 is a partially exploded view of the aspiration device of FIG. 12.
Figure 14:
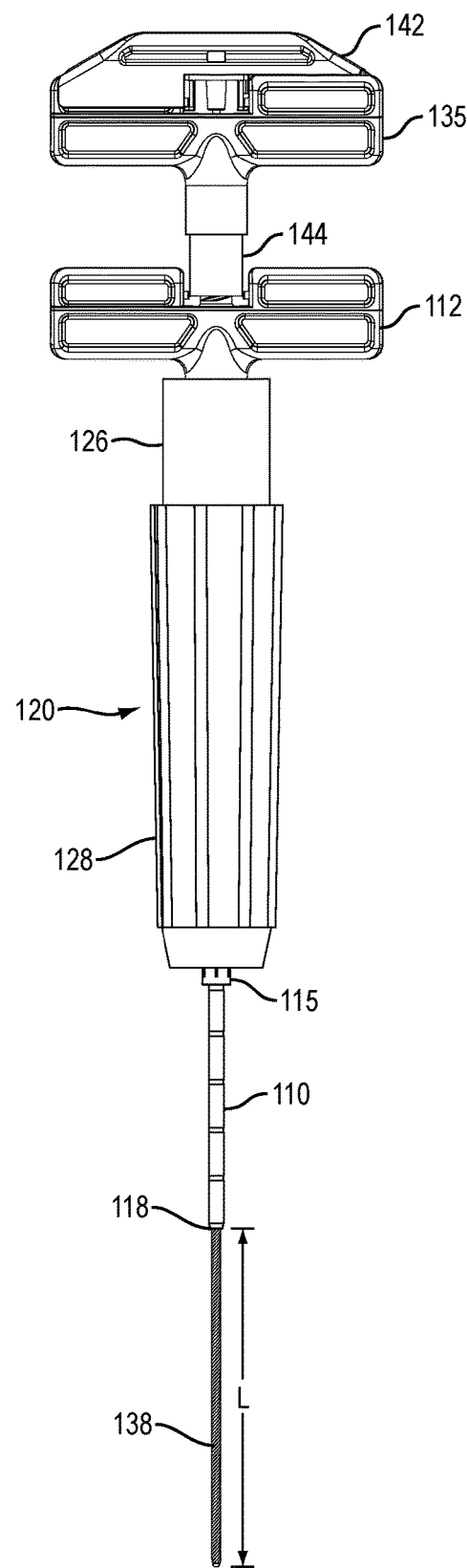

As illustrated in FIG. 13, a blunt stylet 140 having handle 142 is receivable in the aspiration cannula 130. The distal end 134 of the aspiration cannula includes an opening and the blunt stylet 140 is configured to extend through and close the opening, as shown in FIG. 12.

The aspiration needle 104 includes a connector 144 to couple to the introducer needle 102 in an air-tight manner. Connector 144 couples to a corresponding connector 146 provided at handle 112 of the introducer needle. An aspiration handle 135 is connected to the proximal end 132 of the aspiration cannula 104. The aspiration handle 135 includes a port 137 in fluid communication with the aspiration cannula 130 for aspirating or injecting fluid or fluid containing cells, including bone marrow.

The lead screw 124 is hollow and is attached at its head 129 to the introducer handle 112 and needle hub 114. The introducer cannula 106 extends through the hollow lead screw 124.

The aspiration device includes an O-ring 150 between the threaded tube 122 and the outer tube 126 to form the sealing engagement between the threaded tube and the outer tube. O-ring 150 is seated in groove 123 of threaded tube 122 (see, e.g., FIG. 12 and FIG. 17A) and provides a dynamic seal between threaded tube 122 and outer tube 126. The outer tube 126 is attached to the proximal end of lead screw 124 and moves in tandem with the lead screw. The outer tube covers the exposed lead screw. An optional lip (flange or detent) 153 may be provided at the top of outer tube 126 to, for example, retain lead screw 124, as illustrated in FIG. 17A. A further O-ring 152 is provided between outer tube 126 and lead screw 124. O-ring 152 is seated in groove 127 of the lead screw 124 (FIGS. 12 and 17A) and provides a static seal. Additional O-rings 154 and 156 are provided at the upper and lower needle hubs 114 and 115. The O-rings are features that keep portions of the introducer needle, in particular the screw assembly, air tight.

The screw assembly includes a finger grip 128 that extends along a length of the threaded tube 122. As shown in FIG. 16, finger grip 128 is a sleeve that extends around the outer tube 126 and the threaded tube 122. Finger grip 128 includes ridges to facilitate gripping of the introducer needle 102 by the user. As shown in FIGS. 12 and 17C, finger grip 128 is screwed onto outer threads 121 at the distal end of threaded tube 122.

The device shown in FIGS. 12-17C may further include a sharp introducer stylet receivable in the introducer cannula 106. A suitable introducer stylet 7 is shown, for example, in FIGS. 1, 2 and 6, and described above.

It can be appreciated that different needle lengths, materials and dimensions can be used to accomplish the various aspects of the aspiration devices described herein.

Embodiments of the aspiration device and method have several novel and advantageous features. For example, the introducer needle assembly has an optional upper cannula (8, 108) that is not attached to the lower hub (15, 115) and cannula (10, 110). When the screw mechanism is in the collapsed state, the upper cannula preferably butts against the lower hub and cannula, although it need not. Having the upper cannula butt against the lower hub and cannula is advantageous when inserting the introducer needle assembly into bone, for example, to transfer axial force applied via the introducer handle and upper cannula to the lower cannula, since the lower cannula is penetrating the bone. In addition, the upper cannula can act as a guide when inserting the aspiration needle assembly into the introducer needle assembly. Alternatively, a funnel can be provided, e.g., at the lower hub, to guide the aspiration needle into the lower cannula. As the screw mechanism is engaged to reverse the lead screw out of the threaded tube, the upper cannula and lower cannula in the introducer needle assembly separate further from each other. This allows the lower cannula of the introducer needle to remain in the bone while the aspiration cannula is withdrawn from the bone using the screw mechanism. Thus, the wire wound tube of aspiration cannula is not exposed to an environment where air can lead into the wire wound tube during aspiration.

The introducer needle, including the screw mechanism, is air tight so that no air will leak into the wire wound tube (coil spring) that passes through the introducer needle. The threads of the screw mechanism (through which the flexie needle extends) are kept airtight by an O-ring and sliding outer tube. The screw mechanism also functions as an adjustable depth guide to control depth of entry of the flexible aspiration needle into the bone.

Further, an upper portion of the wire wound tube is advantageously supported by a steel cannula jacket to keep it stiff to facilitate the user in advancing the flexible aspiration needle into the body. The flexie needle connects to the introducer needle with a luer connector that couples to the handle of the introducer needle. In one example, the luer connector is secured on the underside of the flexie needle handle with a nut and O-ring feature.

The combination of a wire wound tube, which generally is not air tight, with features that make the environment around the tube (e.g., the introducer needle including the screw mechanism) air tight so that one can aspirate bodily fluid (and tissue, e.g., bone marrow) through the wire wound tube is novel. Using a wire wound tube that is connected to a syringe (or other means of creating suction) where the wire wound tube is inserted through an introducer cannula in order to aspirate bodily fluid through the wire wound tube requires that the wire wound tube be kept air tight as it advances into and out of the introducer cannula so that fluid is aspirated as opposed to air. The embodiments described above use a screw mechanism to advance the wire wound tube into and out of the introducer cannula. An outer tube covers the lead screw and threaded female tube of the screw mechanism and moves in tandem with the lead screw. The outer tube has one or more sealing O-rings that keep the wire wound tube and screw mechanism air tight as the wire wound tube advances and is retrieved through the introducer cannula. Instead of an outer tube, an O-ring may be positioned at a distal end of the lead screw to seal against a non-threaded inner surface of the threaded tube. Such an approach may increase the length of the screw mechanism and hence the overall length of the device. The introducer needle assembly (2, 102) described herein includes an outer tube sealingly engaged with a threaded tube, in a telescoping way, which allows for a shorter overall length of the device while providing for a sufficiently long introducer needle assembly. A length of about 15 cm for an introducer needle has been found useful. A clinician may prefer such a length for orienting the introducer cannula relative to the patient, for leverage, and for ease of manipulation when inserting the introducer cannula into bone. Other ways of sealing are contemplated. For example, as opposed to a threaded lead screw and corresponding threaded female tube, the lead screw and corresponding female tube can be smooth and merely slide together in a sealing manner; and, as opposed to an outer tube that covers the lead screw and female tube, the sliding lead screw and female tube (and the wire wound tube) can be covered with an air tight collapsible plastic covering (i.e. like a bag or bellows) that is connected and sealed on one end to the introducer cannula and on the other end to the handle to which the wire wound tube is connected. The bag can be sealed by something as simple as the compression fit of one or more elastic O-rings that pinch the bag off on either end. Thus, the wire wound tube can advance forward and backward, with the slack in the bag allowing for such forward and backward movement, but air would not enter. Whether using an outer tube and O-rings, a plastic collapsible bag-like covering or another type of covering, the novel insight is that such features enable one to cover and make air tight the moving wire wound tube, which is exposed to air outside the body during the aspiration process, so that one only aspirates bodily fluids and not air.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for aspirating bone marrow, the method comprising:
   inserting an aspiration cannula of an aspiration needle assembly into bone marrow through an introducer cannula placed in a bone, the aspiration cannula having a proximal end and a distal end and including a distal flexible portion that extends along a length of the aspiration cannula and includes a wire wound tube, the aspiration cannula forming a channel for aspirating bone marrow;
   while keeping the wire wound tube air tight, adjusting a length of the aspiration cannula that extends beyond a distal end of the introducer cannula using a screw assembly coupled to the introducer cannula, the screw assembly including a threaded tube and a lead screw receivable in the threaded tube; and
   aspirating bone marrow through the channel.

2. The method of claim 1, wherein adjusting the length of the aspiration cannula that extends beyond the distal end of the introducer cannula is performed by advancing the lead screw into the threaded tube or reversing the lead screw out of the threaded tube.

3. The method of claim 1, wherein the introducer cannula includes an upper cannula coupled to the lead screw and a lower cannula coupled to the threaded tube.

4. The method of claim 1, wherein the aspiration needle assembly includes a blunt stylet having a proximal end and a distal end, the blunt stylet extending through at least a portion of the aspiration cannula.

5. The method of claim 4, further comprising removing the blunt stylet from the aspiration cannula, the aspiration cannula forming the channel for aspirating bone marrow when the stylet is removed.

6. The method of claim 1, wherein inserting the aspiration cannula into the bone marrow includes flexing or bending the aspiration cannula against cortical bone.

7. The method of claim 1, wherein aspirating bone marrow includes retracting the aspiration cannula from the bone.

8. The method of claim 7, wherein retracting the aspiration cannula from the bone includes employing the screw assembly to shorten the length that the aspiration cannula extends beyond the distal end of the introducer cannula.

9. The method of claim 1, wherein aspirating bone marrow is performed while the length of the aspiration cannula that extends beyond the distal end of the introducer cannula is adjusted.

10. The method of claim 1, further comprising, before inserting the aspiration cannula,
    penetrating cortical bone with an introducer needle assembly, the introducer needle assembly including:
        the introducer cannula having a proximal end and a distal end, each end including an opening,
        an introducer stylet having a proximal end and a distal end, the stylet extending through the introducer cannula, the distal end of the stylet extending beyond the distal end of the introducer cannula and including a sharp tip to penetrate bone; and
    removing the introducer stylet.

11. The method of claim 10, further including advancing the introducer needle assembly into the bone to a selected depth before removing the introducer stylet.

12. The method of claim 10, wherein keeping the wire wound tube air tight includes providing a dynamic O-ring seal between the threaded tube and a non-threaded portion of the introducer needle assembly.

13. The method of claim 1, wherein keeping the wire wound tube air tight includes disposing an outer cover around and in sealing engagement with the threaded tube and the lead screw.

14. The method of claim 1, further comprising coupling the aspiration cannula to the introducer cannula in an air-tight manner.

\* \* \* \* \*